United States Patent [19]

Strissel et al.

[11] Patent Number: 5,082,993
[45] Date of Patent: Jan. 21, 1992

[54] HIGH-LYSINE CORN

[75] Inventors: Jerry Strissel, Harlan; George Pollak, Guthrie Center; Bryan Kindiger, Harlan, all of Iowa

[73] Assignee: Orsan, Paris, France

[21] Appl. No.: 388,599

[22] Filed: Aug. 1, 1989

[51] Int. Cl.$^5$ .............................. A01H 5/00; A01H 1/00
[52] U.S. Cl. ........................................ 800/200; 800/250; 800/DIG. 56; 47/58; 47/DIG. 1
[58] Field of Search ............ 47/58, DIG. 1; 800/200, 800/205, 250, DIG. 56

[56] References Cited

PUBLICATIONS

Belousov (1981), Akademii Sel'skokhozyaistvennykh Nauk Imeni V. I. Lenina (No. 4): pp. 14-17.
Klyuchko (1977), IX Meeting of Eucarpia Maize & Sorghum Section, Abstract III, Breeding Maize for Protein Quality.
Tarakanov, et al, (1986), Sbornik Nauchnykh Trudovpo Prikladnoi Botanike, Genetike i Selektsii, No. 105, pp. 58-66.
Witkowski (1989), "The NEB Transcript", pp. 1-7, vol. 2, No. 1.

*Primary Examiner*—Elizabeth C. Weimar
*Assistant Examiner*—Gary Benzion
*Attorney, Agent, or Firm*—Cooley Godward Castro Huddleson & Tatum

[57] ABSTRACT

An inbred corn plant containing dominant genetic information that expresses high protein and increased lysine levels in corn kernels produced by the plant is provided. The genetic information in the plant can be used to produce novel inbred corn lines and hybrid corn lines containing high protein and lysine levels both by established plant breeding techniques and other techniques of genetic manipulation.

5 Claims, No Drawings

HIGH-LYSINE CORN

INTRODUCTION

1. Technical Field

This invention is related generally to the production of maize, commonly known in the United States as corn, and more particularly to maize containing genetic material capable of causing higher than normal production of protein and lysine, and to the unique genetic material itself.

2. Background

Single-cross hybrid corn is produced by crossing two homozygous inbred lines. Homozygosity in an inbred line is achieved by repeated inbreeding; in general, by the seventh or eighth generation the inbred line is considered genetically pure. Plant breeders basically have two sources of germplasm from which to develop new inbreds. They include adapted corn belt germplasm and exotic germplasm. The steady increase in corn yield in the United States over the past fifty years has been accomplished almost exclusively with adapted germplasm.

Industry's needs for corn are becoming increasingly segmented, opening new markets for corn that has specialized characteristics. The grain processing industry, especially the dry millers, are interested in new hybrids with grain that has an increased amount of hard endosperm and which can still be grown competititively against current commercial hybrids. The livestock industry, already the largest user of corn, has a potential for value-added, nutritionally improved corn. Globally, about two thirds of total maize production is used for livestock feed (Glover, D. V. and Mertz, E. T. (1987) *Agronomy Monograph*, 28: 183–336). Maize is thus an important food material which supplies 19 percent of the world's food calories. Corn also contributes 42 million tons of protein a year, which represents 15 percent of the world's annual production of food-crop protein. Understandably, high grain yields are the objectives of most corn improvement programs, and breeding for nutritional quality or special purposes has been of minor importance because of the lack of incentives, the lack of communication with the end-user for specific demands, and the lack of breeding efforts in using exotic germplasm which can offer some unique traits.

Accordingly, there remains a need for developing unique inbred lines of maize that offer genetic diversity and special traits such as increased amounts of hard endosperm in the grain and increased nutritive values such as high lysine. Additionally, there remains the need to develop the genetic material that can control the lysine content in a dominant and more stable manner than the previously known recessive opaque-2 (O2) system, the best known genetic source of high-lysine corn.

SUMMARY OF THE INVENTION

It is the object of the present invention to provide an inbred corn line that is significantly different genetically from commercially available adapted inbred corn lines.

It is also an object of this invention to demonstrate that the use of this inbred increases the protein and lysine content of resulting single-cross hybrids.

It is still a further object of this invention to demonstrate that the nutritive value of a resulting hybrid using this inbred is increased as measured by a significant increased rate of gain in livestock.

These and other objects of the invention have been accomplished by providing an inbred corn line (identified as WIL500), hybrid corn lines that have the WIL500 line as a parent, and other plant forms, such as cell lines and other inbred corn lines, that contain the genetic information of the WIL500 line that relates to high lysine and protein production. Characteristics of the genetic information are discussed in more detail below.

Seeds of the WIL500 inbred corn line plant have been deposited with the Plant Variety Protection Office, NAL Building, Room 500, 10301 Baltimore Boulevard, Beltsville, Md. 20705-2351 and have received CORN, FIELD, Application No. 8900156. Seeds of the WLL500 inbrid corn line plant have been deposited with the American Type Culture Collection (ATCC), 12301 Parklawn Drive, Rockville, Md. 20852 as ATCC No. 40844.

DETAILED DESCRIPTION OF THE INVENTION

WIL500 was derived as a self out in an exotic corn breeding experiment carried out at Wilson Hybrids, Ind., of Harlan, Iowa. This breeding program used corns primarily from tropical origins, especially sub-tropical white dent germplasm, to screen for useful genetic material capable of improving inbred corn lines used in producing hybrids for the North American corn belt and for other purposes.

A pedigree breeding method was used for the development of WIL500. In each of the six selfing generations during development, the line that eventually became WIL500 was selected for on a line-per-se basis for agronomic characteristics and specific traits that are discussed below. During the last four selfing generations, the line that became WIL500 was also evaluated in hybrid combination with other inbreds. In hybrid combination, the line was evaluated in replicated yield trials at different locations for grain yield, protein quantity, protein quality, hybrid agronomic traits, and stability of traits.

The initial multiplication of WIL500 was made by shelling all the seed from a single ear of corn selected by the selfing process as described above and planting these seeds in a nursery block. All of the plants that resulted were selfed by hand pollination, and at harvest the seeds from these ears were bulked and called WIL500. Using this initial seed bulk, subsequent seed multiplication was made in an isolation increase field. No variants were observed during the seed increase of WIL500. The inbred plants appeared stable and uniform in the seed increase fields.

WIL500 was compared to a public released corn inbred line called AR266 that is typical of U.S. corn belt inbred lines to demonstrate the particular characteristics of WIL500. Twenty to twenty-five measurements were made per trait on each of these inbreds. From these measurements, means, variances and t values were calculated. The t values were calculated by the following formula:

$$t \text{ calc.} = \frac{x_1 - x_2}{\sqrt{\frac{s^2_1 + s^2_1}{n}}}$$

where: $\bar{x}_1$, $\bar{x}_2$ = mean 1 and mean 2 respectively; $s^2_1$, $s^2_2$ = variance 1 and variance 2 respectively; and n = number of measurements per mean.

Statistical differences between the means were determined by the t values for n-1 degrees of freedom at the 5% level of probability. Statistically significant differences between the means of traits of WIL500 and AR266 are marked as significant in Table 1.

TABLE 1

Comparison of WIL500 to AR266

| Character | Obser./inbred | Mean WIL 500 | Mean AR 266 | Variance WIL 500 | Variance AR 266 | Calc t value |
|---|---|---|---|---|---|---|
| Tassel branches/tassel | 25 | 9.00 | 11.88 | 8.42 | 8.28 | 3.524* |
| Tassel Branch Angle | 25 | 16.80 | 34.60 | 81.00 | 133.17 | 6.081* |
| Peduncle Length cm | 25 | 2.88 | 3.24 | 1.86 | 1.27 | 1.017 |
| No. of leaves/plant | 25 | 14.00 | 13.32 | 1.42 | 1.14 | 2.125* |
| Leaf Angle | 25 | 26.60 | 29.00 | 84.82 | 127.08 | 0.824 |
| Ear Leaf Length cm | 25 | 76.28 | 72.88 | 36.88 | 24.28 | 2.174* |
| Ear Leaf Width cm | 25 | 8.60 | 8.84 | 0.33 | 0.47 | 1.342 |
| Husk Leaf Length cm | 25 | 1.24 | 0.60 | 0.19 | 0.58 | 3.647* |
| Plant Height cm | 25 | 129.88 | 143.92 | 66.36 | 636.33 | 2.648* |
| Ear Height cm | 25 | 37.84 | 48.00 | 27.81 | 106.67 | 4.381* |
| Top Ear Internode Length cm | 25 | 5.84 | 19.32 | 11.72 | 25.14 | 11.102* |
| Husk Extension cm | 25 | 7.56 | 7.72 | 4.09 | 0.96 | 0.356 |
| Shank Length cm | 25 | 10.20 | 13.40 | 1.75 | 7.50 | 5.261* |
| Shank Internodes | 25 | 9.76 | 10.80 | 1.36 | 1.17 | 3.269* |
| Ear Length cm | 20 | 14.05 | 12.15 | 1.94 | 1.50 | 4.581* |
| Ear Weight gm | 20 | 30.20 | 59.50 | 145.75 | 389.74 | 5.662* |
| Kernel Rows/Ear | 20 | 13.30 | 13.20 | 2.22 | 2.27 | 0.211 |
| Ear Diameter mm | 20 | 35.75 | 35.60 | 9.46 | 4.36 | 0.180 |
| Cob Diameter mm | 20 | 27.50 | 21.95 | 7.84 | 1.31 | 8.205* |
| 100 Kernel Weight gm | 20 | 23.58 | 25.28 | 12.37 | 9.25 | 1.635 |
| % Round Kernels | 20 | 78.75 | 56.60 | 315.25 | 387.62 | 3.736* |
| Kernel Thickness mm | 20 | 4.35 | 4.90 | 1.61 | 1.57 | 1.379 |
| Kernel Width mm | 20 | 7.60 | 7.30 | 0.88 | 0.43 | 1.172 |
| Kernel Length mm | 20 | 6.90 | 8.20 | 0.52 | 0.80 | 5.060* |
| No. of Tillers/Plant | 25 | 0 | 0 | 0 | 0 | 0 |

*Significant

Additionally, the following differences, although not tested for statistical significance, where observed between WIL500 and AR266. as compared to AR266, WIL500 flowers two days later, forms kernel black layer five days later, reaches 25% kernel moisture two days later, has less pollen shed, has a lighter green leaf color, has fewer marginal leaf waves amd ore longitudinal creases. WIL500 has a white cob, wherereas AR266 has a red cob.

A number of the characteristics of WIL500 and its hybrids are of particular advantage because of requirements of the milling industry. Currently, some dry millers pay a premium for corn that meets certain standards in kernel characteristics. Acceptable corn must have the following characteristics:

1. A high percent of bright-yellow, hard-endosperm starch
2. A high percent of corn oil
3. Uniform, large-size kernels
4. An attractive, bright yellow color Acceptable corn hybrids on the market today have a range of 56 to 58.8% hard endosperm (Table 2). Dry millers have expressed interest in seeing future hybrids developed that would have kernels that attained 62% hard endosperm and have yields within 10% of leading commercial hybrids.

TABLE 2

Comparative Milling Characteristic of Previous Wilson Corn Hybrids

| Description | 1500b | 1700 | 1700b | 1800b | 2100 | 2300 |
|---|---|---|---|---|---|---|
| Test Wt. lbs/bu | 58.5 | 59.0 | 59.3 | 58.3 | 59.7 | 59.3 |
| % Small Kernels | 3.4 | 5.6 | 7.7 | 5.8 | 2.4 | 4.1 |
| % Hard Endosperm | 57.0 | 57.3 | 58.8 | 56.0 | 58.8 | 57.7 |
| % Floury Endosperm | 13.8 | 14.6 | 13.8 | 14.7 | 14.3 | 14.2 |
| % Germ | 14.9 | 14.9 | 13.5 | 14.7 | 13.8 | 13.9 |

A selective screening process was initiated on the testing phase of 1500 hybrids in the breeding program. The criteria consisted of the following:

1. Protein values to exceed 10%.
2. Test weight to exceed 59 lbs./bu. (normal=56 lbs./bu.)
3. Yield comparable to those of standard corn lines.
4. Plants tolerant to anthracnose.
5. Plants tolerant to stalk rot, especially fusarium.
6. Kernels to have a high percent of hard endosperm.

A sample of a hybrid having WIL500 as a parent, designated as T2021, was taken to a dry miller for analysis. The results (Table 3) indicated that this grain had a significant increase in the amount of hard endosperm. In addition, yield of the T2021 was comparable to leading Wilson hybrids.

TABLE 3

Comparative Milling Characteristics of Wilson Corn Hybrids

| Description | 1700 | 1700b | 2100 | 2300 | T2021 |
|---|---|---|---|---|---|
| Test Wt. lbs/bu | 59.0 | 59.3 | 59.7 | 59.3 | 63.0 |
| % Small Kernels | 5.6 | 7.7 | 2.4 | 4.1 | 0 |
| % Hard Endosperm | 57.3 | 58.8 | 58.8 | 57.7 | 64.2 |
| % Floury Endosperm | 14.6 | 13.8 | 14.3 | 14.2 | 14.0 |
| % Germ | 14.9 | 13.5 | 13.8 | 13.9 | 10.0 |

Protein and Lysine Evaluation

During the selective screening process discussed above, it was discovered that T2021 not only had high levels of hard endosperm, it had significantly increased protein and lysine levels compared to regular corn (Table 4). All grain samples were obtained from a replicated yield trial, which means that the traits of higher protein and lysine are dominant since this corn had not been isolated during growth from other sources. Isolation of growing corn from other corn fields is required if a recessive trait is to be expressed since otherwise cross pollination from the other corn will mask the effects of the recessive trait.

TABLE 4

Composition of Wilson T2021 vs. Regular Corn[1]

| Characteristic | Regular Corn | Wilson T2021 |
|---|---|---|
| Crude Protein | 7.0 to 9.0 | 10.2 to 10.5 |
| Lysine (%) | 0.23 | 0.38 (kernel) |
| Oil (%) | 3.3 to 4.0 | 4.0 |
| % Hard Endosperm | 47 to 58 | 64.2 |
| % Floury Endosperm | 14 to 15 | 14 |
| % Germ | 14 to 19 | 10 |
| Test Wt. lbs/bu | 55 to 60 | 63 |

[1]Range of values for commercial yellow dent corn were obtained from grain analysis completed by A and L Laboratories and by Lincoln Grain on hybrids that are representative of the majority of hybrids used in the midwest. Values are based on 12% moisture. The protein, lysine, and oil values are very representative of published values which are discussed in "Corn: Chemistry and Technology," S. A. Watson and P. E. Ramstad, 1987, American Association of Cereal Chemists, Inc., St. Paul, Minnesota.

In addition to T2021, several other genetic combinations were made with the inbred line WIL500 and tested for grain protein levels in several experiments. Three WIL500 combinations were compared against a regular commercial corn for protein levels under different plant populations and different fertilizer rates. In this trial, all combinations of WIL500 crossed by any adapted foundation inbred line had significantly higher grain crude protein levels than commercial corn (adapted foundation line × adapted foundation line) under all population and fertilizer rates tested (Table 5).

TABLE 5

Grain Protein Analysis of Different Combinations of WIL500 Compared to Wilson 1700

| Product I.D. | Pedigree[1] | Pop.[2] | Fert.[3] Rate | % H$_2$O | Yield Bu/A | 0% H$_2$O Prot. | Oil |
|---|---|---|---|---|---|---|---|
| T3138 | WIL500 | 17,000 | 1x | 15.1 | 158.95 | 12.5 | 5.1 |
|  | × | 23,000 | 1x | 16.0 | 179.77 | 12.3 | 4.6 |
|  | F. Line | 17,000 | 1x + 80 | 16.4 | 152.24 | 12.7 | 4.9 |
|  | A | 23,000 | 1x + 80 | 16.8 | 158.45 | 12.7 | 4.9 |
| T3166 | WIL500 | 17,000 | 1x | 21.0 | 136.70 | 13.3 | 4.2 |
|  | × | 23,000 | 1x | 20.4 | 164.56 | 12.8 | 4.6 |
|  | F. Line | 17,000 | 1x + 80 | 21.2 | 159.00 | 13.7 | 4.5 |
|  | B | 23,000 | 1x + 80 | 20.7 | 161.96 | 13.1 | 4.6 |
| T3127 | WIL500 | 17,000 | 1x | 16.6 | 152.32 | 12.4 | 4.5 |
|  | × | 23,000 | 1x | 16.9 | 153.90 | 12.3 | 5.2 |
|  | F. Line | 17,000 | 1x + 80 | 15.7 | 138.18 | 12.9 | 4.5 |
|  | C | 23,000 | 1x + 80 | 15.5 | 145.91 | 12.4 | 4.8 |
| Wilson 1700 | F. Lines G × H | 17,000 | 1x | 15.2 | 162.52 | 10.4 | 4.1 |
|  |  | 23,000 | 1x | 14.9 | 178.68 | 9.6 | 4.2 |
|  |  | 17,000 | 1x + 80 | 14.1 | 166.85 | 10.9 | 4.3 |
|  |  | 23,000 | 1x + 80 | 14.8 | 170.22 | 10.1 | 4.1 |

L.S.D. = 0.34 (0.05)
[1]F. Line = Foundation inbred line
[2]Pop. = Plant population rate per acre
[3]Fert. Rate = Fertilizer rate;
1x = standard rate of 160 pounds of actual nitrogen;
1x + 80 = 160 pounds nitrogen plus 80 pounds of nitrogen An additional trial was conducted in three different Iowa research locations to compare the crude protein content of T2021 to the standard commercial corn Wilson 1700 across a range of environmental conditions. In all locations, T2021 had significantly more grain protein than Wilson 1700 (Table 6).

TABLE 6

Grain Protein Analysis of T2021 (Wilson × F Line D) Compared to Wilson 1700 Across Three Research Locations in Iowa

| | Pedigree | Harlan 0% H$_2$O Pro (%) | Clarinda 0% H$_2$O Pro (%) | N. Sharon 0% H$_2$O Pro (%) | Mean* 0% H$_2$O Pro (%) |
|---|---|---|---|---|---|
| T2021 | WIL500 × F Line D | 11.2 | 11.2 | 11.7 | 11.4 |
| 1700 | LH119 × LH51 | 9.7 | 9.7 | 10.3 | 9.9 |

*Mean of 7 replications

Seed of the hybrid T3166 was collected and analyzed (in comparison to generic corn) for nutrient composition. The results definitely indicated a significant increase in protein and lysine levels (Table 7).

TABLE 7

Nutrient Composition of Grains Involved in the High Protein Corn Evaluation Study[1]

| Component | Generic Yellow Corn[2] | Exper. high protein corn (T3166) |
|---|---|---|
| Metabolizable energy | | |
| KCal/lb | 1530 | 1530 |
| KCal/kg | 3370 | 3370 |
| Fat % | 3.8 | 3.8 |
| Linoleic acid % | 1.9 | 1.9 |
| Crude Protein % | 8.9 | 11.2 |
| Lysine % | .24 | .32 |

[1]Nutrient composition values are based on 12% moisture
[2]Generic corn is from the 1987 crop of commercial yellow dent corn representative of corn used in Nebraska for feeding livestock the grain of the inbred line WIL500 was also tested for crude protein and lysine levels and compared to other inbred lines (Table 8). The results clearly indicated that the lysine level of WIL500 was similar to that of inbred lines that possessed the recessive opaque-2 gene, and far superior to standard foundation inbred lines. The previous analysis (Table 7) clearly indicated that hybrids with WIL500 did have a significantly higher lysine content. An additional important fact is that the increase in protein and lysine in the hybrid was obtained without isolating the field. This is a significant advantage over use of the opaque-2 system, as the recessive opaque-2 system (O2) requires field isolation.

TABLE 8

Protein and Lysine Analysis of the Grain of Various Inbreds and of Hybrid Combinations

| Product I.D. | Protein (%) | Lysine (%) |
|---|---|---|
| WIL500 (Harlan Nursery) | 10.38 | 0.44 |
| Tuxpeno QPM 02 | 10.06 | 0.46 |
| IPTT42 QPM 02 | 9.76 | 0.39 |
| Mo17 02 | 11.18 | 0.47 |
| Foundation Line A | 9.08 | 0.31 |
| Foundation Line B | 9.03 | 0.29 |
| Foundation Line C | 9.28 | 0.31 |

To determine if the increased protein levels of the experimental corn T3166 (WIL500×adapted inbred B) also increase nutritive value, two feeding trials were conducted. The first used grains in diets considered low in protein for starting chicks (18.4% protein). The rationale for this was that if the experimental corn was truly higher in protein, chicks would gain more weight. In trial two, recommended (NRX, 1984) protein levels (22% in the starter, 19% in the grower) were used, and the birds were fed to 42 days of age. In each trial, body weight gain and feed efficiency were used as response criteria.

Results of feeding trials one and two are shown in Table 9. In the first trial, chicks receiving the experimental high protein corn diet gained about 40 grams (about 0.10 pound) more weight than chicks fed diets with the other grain sources. Therefore, this cultivar of corn can be called high protein since the protein level is great enough to end the need for soybean meal, and chicks still grow at a fast rate. In trial two, there were no significant differences in 21-day weight gains (these diets contained recommend instead of low protein levels). However, at 42 days the birds fed diets containing high protein corn had gained 117 grams and 70 grams more (about 0.25 and 0.15 pound) than birds fed generic corn and grain sorghum diets, respectively.

TABLE 9

Performance of Chicks Fed High Protein Corn, Generic Corn, and Grain Sorghum

| | Trial 1 | | Trial 2 | | | | |
|---|---|---|---|---|---|---|---|
| | Body wt gain (grams)[1] | Feed/gain ratio | Body wt gain (grams)[2] | | Feed/gain ratio | | Shank color |
| Treatment | Day 21 | Day 21 | Day 21 | Day 42 | Day 21 | Day 42 | Day 42 |
| Generic Corn | 585a | 1.68b | 571a | 1633a | 1.64b | 2.00b | 7.3c |
| Experimental High Protein Corn (#3186) | 627b | 1.57a | 590a | 1750b | 1.57a | 1.96a | 6.5b |
| Sorghum (NC + 271) | 588a | 1.61ab | 596a | 1680a | 1.54a | 1.94a | 1.0a |

[1]Each value is the average of 5 replicate pens containing 6 Vantress X Arbor Acre chicks per pen.
[2]Each value is the average of 5 replicate pens of males and 5 replicate pens of females containing 6 Vantress X Arbor Acre chicks per pen.
a, b, c Values within the same column which are followed by different subscripts are statistically different (P < .05).

In summary, an experimental high protein corn with increased lysine levels improved performance of broiler chicks receiving both low and recommended or standard protein levels in their diets. High protein corn has the potential to reduce the need for soybean meal in poultry diets.

Restriction Fragment Length Polymorphism

Restriction fragment length polymorphism (RFLP) has been extensively used in human and plant genetics for varietal and parental lineage identification. A complete description of this technology is described in Soller, M. and J. S. Bockmann, *Genetic polymorphism in varietal identification and genetic improvment*, (1988) *Theor. Appl. Genet.* 67: 25-33 and Heleutjaris, T., *A genetic linkage map of maize based on RFLPs* (1987) TIG 3: 217-221. In this technology DNA is isolated from the seedlings obtained after planting seed of the corn line to be tested, using published techniques. After restriction with HIND III, a commercially available restriction enzyme, the DNA is tested with DNA probes. In the case reported here UMC probes and BNL probes were obtained from Dr. D. Hoisington, 303 Curtis Hall, University of Mo., Columbia, Mo. 65211 and Dr. F. A. Burr, Biology Department, Brookhaven National Laboratory, Upton, N.Y. 11973. In addition to WIL500 line, DNA was also extracted from MO17, B73 and LH123 corn homozygous lines. The size of the DNA fragments reacting with the probes (Table 10) indicate a specific pattern of the WIL500 line which identify the genetic material of this corn line.

TABLE 10

Characterization of the Line WIL500

| | Length of Restriction Fragment in Kb | | | |
|---|---|---|---|---|
| Probe | WIL500 | LH123 | MO17 | B73 |
| UMC83 | 10 | 3.9 | 9.8 | 2.7 |
| BNL12.06 | 4.1 | 4.1 | 18.4 | 3.7 |
| UMC5 | 2.7 | 4.2 | 2.6 | 2.6 |
| UMC34 | 7.5 | 18.0 | 4.8 | 5.6 |
| UMC131 | 3.8 | 3.8 | — | — |

TABLE 10-continued

Characterization of the Line WIL500

| Probe | Length of Restriction Fragment in Kb | | | |
|---|---|---|---|---|
| | WIL500 | LH123 | MO17 | B73 |
| UMC139 | 5.3 | 5.3 | 6.4 | 4.5 |
| BNL8.45 | 11.0 | 11.0 | 8.6 | 8.6 |
| UMC10 | 5.3 | 7.3 | 7.2 | 5.2 |
| UMC102 | 6.7 | 6.7 | 5.7 | 5.5 |
| UMC19 | 3.9 | 2.3 | — | — |
| UMC56 | 6.2 | 6.2 | 2.3 | 2.3 |
| UMC151 | 2.3 | 4.4 | 2.7 | 2.7 |
| BNL14.07 | 10.0 | 10.0 | — | — |
| BNL15.21 | 7.0 | 20.0 | — | — |

Characteristics of WIL500 are as follows:
Plant color—dark green
Emergence—Average to good (similar to B73)
Vigor—Average to good (similar to B73)
Stalk
  Height (cm)—129.88
  Ear Height (cm)—37.84
  Anthycyanin—Stalks are green with no visual evidence of anthocyanin pigment
  Tillers/Plant—0
  Brace roots—Good brace root development at the base. Color=green
Leaves
  Angle—26.60
  Number/Plant—1400
Leaf Sheath
  Anthocyanin—Leaf sheath is dark green with no visual evidence of anthocyanin pigment
  Pubesence—Heavy (similar to OH26)
  Width (cm)—8.60
  Ear leaf length (cm)—76.28
Tassel
  Length (cm)—23.0
  Branch angle (cm)—16.80
  Branching—9.00
  Anther color—Green
Peducle length (cm)—2.88
Ear
  Silk color—Green
  Husk bracts—Buff in color
  Ear/Stalk—one
  Length (cm)—14.05
  Weight (gm)—30.20
  Shape—Conical
  Diameter (mm)—35.75
  Top ear internode length (cm)—5.84
  Kernel Rows/Ear—13.30
  Shank length (cm)—10.20
  Shank internodes—9.76
  Husk number —9-11
  Husk extension (cm)—7.56
  Husk leaf length (cm)—1.24
  Husk width (cm) —5
  Cob color—White
  Cob diameter (cm)—27.50
Kernel
  Type—Flint
  Color—Yellow
    Cap—Medium yellow
    Sides—Dark yellow
  Thickness (mm)—4.35
  Form—78.75% round kernels
  Width (mm)—7.60
  Length (mm)—6.90
  Weight 100 Kernels (gm)—23.58
  Texture—>58% of a very hard endosperm with very little white floury starch present
Pollen Shed
  Days—75
  Degree Days—1745
50% Silk
  Days—79
  Degree days—1765
  Shank diameter (cm)—1.5
  Glume Color—Green
  Glume band—Red
  Tassel—branch angle —16.8°
  Brace root color—green
Days to flower—75-79
Days to black layer—148 (from emergence)
Days to 25% kernel moisture—158 (from emergence)

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A corn plant of the line WIL500 wherein said plant produces corn kernels containing at least 10.5% crude protein and 0.31% lysine based on 12% kernel moisture.

2. Seed produced by cultivation of the corn plant of claim 1.

3. A hybrid corn plant, wherein at least one ancestor of said hybrid corn plant is the corn plant of claim 1.

4. The inbred corn plant of claim 1 wherein said plant is derived from the seed type deposited with the American Type Culture Collection (ATCC) and having the ATCC No. 40844 or the Plant Variety Protection Agency and having Application No. 8900156.

5. Seed produced by cultivation of the hybrid plant of claim 3.

* * * * *